US012765976B2

(12) United States Patent
Nulty et al.

(10) Patent No.: US 12,765,976 B2
(45) Date of Patent: Oct. 20, 2026

(54) METHOD OF GENERATING MANUFACTURING PARAMETERS DURING A DENTAL PROCEDURE FOR A DENTAL PROSTHESIS

(71) Applicants: Adam Brian Nulty, Bury (GB); Quintus Van Tonder, Norwich (GB)

(72) Inventors: Adam Brian Nulty, Bury (GB); Quintus Van Tonder, Norwich (GB)

( * ) Notice: Subject to any disclaimer, the term of this patent is extended or adjusted under 35 U.S.C. 154(b) by 342 days.

(21) Appl. No.: 18/537,622

(22) Filed: Dec. 12, 2023

(65) Prior Publication Data

US 2024/0189076 A1 Jun. 13, 2024

(30) Foreign Application Priority Data

Dec. 13, 2022 (GB) .................................... 2218753
Dec. 14, 2022 (EP) .................................... 22213439

(51) Int. Cl.
*A61C 13/00* (2006.01)
*A61C 13/107* (2006.01)
*A61B 1/24* (2006.01)

(52) U.S. Cl.
CPC ...... *A61C 13/0001* (2013.01); *A61C 13/0004* (2013.01); *A61B 1/24* (2013.01)

(58) Field of Classification Search
CPC ............ A61C 13/0004; A61C 13/0001; A61C 13/0006
See application file for complete search history.

(56) References Cited

U.S. PATENT DOCUMENTS

| | | | | |
|---|---|---|---|---|
| 2007/0207441 | A1 | 9/2007 | Lauren | |
| 2013/0122468 | A1* | 5/2013 | Abrams | A61B 5/4547 433/215 |
| 2013/0260340 | A1* | 10/2013 | Stegall | A61B 6/481 433/217.1 |
| 2020/0066391 | A1* | 2/2020 | Sachdeva | G16H 20/40 |
| 2021/0128281 | A1* | 5/2021 | Peleg | A61B 1/24 |
| 2023/0035538 | A1* | 2/2023 | Marshall | A61C 9/0053 |

FOREIGN PATENT DOCUMENTS

| | | |
|---|---|---|
| CN | 115607322 A | 1/2023 |
| ES | 2548331 | 10/2015 |
| ES | 2733559 | 11/2019 |
| RU | 2020124542 | 12/2020 |
| WO | 2022/174165 | 8/2022 |

* cited by examiner

*Primary Examiner* — Deirdre D Hatcher
(74) *Attorney, Agent, or Firm* — Adam Warwick Bell

(57) ABSTRACT

The present invention relates to a method of generating manufacturing parameters during a dental procedure to construct a dental prosthesis, the method comprising the steps of: a) intra-orally scanning a patient to generate intra-oral data; b) extra-orally scanning the patient during a mandibular motion to generate dynamic extra-oral maxillofacial data; c) resolving the intra-oral data with the dynamic extra-oral maxillofacial data to generate a combined data model; d) generating a model representation of the dental prosthesis based on the combined data model and displaying the model representation to a user; and e) generating manufacturing parameters based on the combined data model.

19 Claims, 6 Drawing Sheets

(a) (b)

METHOD OF GENERATING MANUFACTURING PARAMETERS DURING A DENTAL PROCEDURE FOR A DENTAL PROSTHESIS

CROSS-REFERENCES TO RELATED APPLICATIONS

This application claims priority to a British application GB2218753.8 filed Dec. 13 2022, and from European application EP22213439.7 filed Dec. 14 2022, both of which are hereby incorporated herein by reference.

FIELD OF THE INVENTION

The present invention relates to a method of generating manufacturing parameters during a dental procedure for a dental prosthesis, particularly but not exclusively for use in restorative dental treatments including orthodontic treatments. The invention further relates to an in-situ dental prosthesis manufacturing system which is capable of implementing the said method.

BACKGROUND OF THE INVENTION

Computer aided design (CAD) and computer aided manufacture (CAM) in the manufacture of dental prosthesis has gained increased momentum in recent years. CAD/CAM processes offer many potential benefits over traditional methods, including increased quality of the final prosthesis, removal of the gag-inducing impressions, and the possibility of a reduction on the typical three-week lead time on the manufacture of the final prosthesis.

The existing process for CAD/CAM manufacturing of bespoke dental implants is as follows. A three-dimensional static digital impression of the mouth is taken, and the relevant data is exported. This is sent to a CAD/CAM machine off site for manufacture. The process is slow, mainly due to the need for multiple manual steps in current CAD/CAM processes including, manual image processing, manual identification of the tooth margins and the need to accurately scan and capture the surrounding and occlusive teeth.

Furthermore, CAD software requires a high-performance computing device, with the set-up thereof being expensive and generally only installed on a single computer.

It is an object of the present invention to reduce or substantially obviate the aforementioned problems.

BRIEF SUMMARY OF THE INVENTION

According to a first aspect of the invention there is provided a method of generating manufacturing parameters during a dental procedure for a dental prosthesis. The method comprises the steps of: a) intra-orally scanning a patient to generate intra-oral data; b) extra-orally scanning the patient during a mandibular motion to generate dynamic extra-oral maxillofacial data; c) resolving the intra-oral data with the dynamic extra-oral maxillofacial data to generate a combined data model; d) generating a model representation of the dental prosthesis based on the combined data model and displaying the model representation to a user; and e) generating manufacturing parameters based on the combined data model; and further comprising a step prior to step c), of identifying the patient using facial recognition based on the dynamic extra-oral maxillofacial data and/or the static extra-oral maxillofacial data; and a further step after step d), of exporting the intra-oral data and associating it with a dental record of the patient.

The present invention seeks to combine digital moulds of the tooth or teeth of interest from scans taken intra-orally with scans taken extra-orally while the mandible is in motion. By combining at least these two datasets, which may be referred to as digital moulds, allows accurate determination of the prosthesis in terms of desired bite and interferences, occlusion, contact with surrounding teeth and tooth margins, at least. Such combined data models, inform a much more accurate model with reduced user input for significantly reduced processing time and demands on skilled professionals in the field of both dentistry and image analysis and manipulation.

Preferably, during step c), more than one said combined data model may be generated. During step d), more than one said model representation of the dental prosthesis may be generated based on each of the more than one combined data models respectively. A further step after step d) and before step e) may also be provided, the step involving the selection of one representation of the dental prosthesis. During step e), manufacturing parameters may then be generated based on the combined data model of the selected one representation. In this instance, multiple options of model representations and associated combined data models are generated which may differ by tooth shape whilst also offering the correct bite. This may be presented to a user as simple on-screen prompts. By providing a selection of possible prostheses to a user, which may be the patient, dental surgeon and/or dental technician, can minimise the risk of manufacturing a prosthesis which may then be rejected by a user.

Another benefit not fully realised by current CAD/CAM systems includes the possible integration of such systems with a patient's dental records.

In order to help minimise the risk of manufacturing a prosthesis from the generated manufacturing parameters which may not be fit for purpose, a step after step d) and before step e) of amending the combined data model based on amendments made to the model representation or the selected one representation of the dental prosthesis displayed to the user.

Optionally, during step b), the mandibular motion is facilitated by a contrast-enhancing medium. The contrast-enhancing medium may be a liquid or a solid deformable tablet.

The contrast-enhancing medium aids the ability for algorithms to identify soft tissue and hard tissue margins for the restoration.

Beneficially, during step a), the generation of intra-oral data may include intra-orally scanning a single tooth of the patient, providing a high-quality digital mould of the tooth of interest which may be the tooth being restored.

Additionally, or alternatively, during step a), the generation of intra-oral data includes intra-orally scanning a full arch of the patient's mandibular teeth and/or maxillary teeth. Full arch scans provide data that the combined data model can use to calculate the required contact that a prosthesis may need with surrounding, or adjacent teeth.

In order to inform the manufacture of a prosthesis of the correct colouring, the intra-oral data may include data indicative of the patient's tooth colouring.

Static extra-oral maxillofacial data may also inform the combined data model by step b) further including extra-orally scanning the patient while a mandible of the patient is in a closed position, and during step c) the combined data model is based on resolving the intra-oral data with both the dynamic and static extra-oral maxillofacial data. Whilst it is acknowledged that the dynamic extra-oral data could be used to generate static extra-oral data, by extra-orally scanning the patient when their mandible is in a closed position can help inform the correct bite, interferences and/or occlusion when the patient's mandible is in a restful state, which may differ from when the mandible is in motion.

Beneficially, manufacturing parameters may be determined for many different types of prosthesis, including a veneer, a crown, an inlay, an implant, and a bridge. In other instances, the type of prosthesis may include inlays, onlays, veneers, crowns, fixed partial dentures, implant abutments, and full-mouth reconstructions. Such a versatile method can help achieve sufficient throughput for a practice to warrant investment into such CAD/CAM processes which can have significant start-up costs.

According to the present invention, the method may further comprise a step prior to step c), of identifying the patient; and a further step after step d), of exporting the intra-oral data and associating it with a dental record of the patient. This process could be further automated by identifying the patient prior to step c) and after step b) using facial recognition based on the dynamic extra-oral maxillofacial data. Alternatively, such facial recognition may in some instances be based on the static extra-oral maxillofacial data. In a similar vein, a further step may be provided after step d), of exporting the combined data model and associating it with the dental record of the patient. Additionally, patient-dental surgeon discussions may also be captured using the present invention, automating the capture and storage of patient consent, further streamlining dental procedures.

Optionally, a step before step e) may be provided, of prototyping the model representation or the one selected model representation of the dental prosthesis. Such prototyping may be realised by means of additive manufacturing the model representation or the one selected representation of the dental prosthesis. By prototyping the model representation or the one selected representation, the prosthesis also has the option of being manufactured in a conventional manner.

Additionally, or alternatively, such a prototype can be used to optimise the model representation, informing amendments which may be made to the model representation and associated combined data model.

According to a second aspect of the invention there is provided an in-situ dental prosthesis manufacturing system. The system comprises: an intra-oral scanning device; an extra-oral scanning device; a computing device in communication with both the intra-oral scanning device and the extra-oral scanning device, the computing device having a display and a processor; and a manufacturing device in communication with the computing device; wherein the intra-oral scanning device is configured to generate intra-oral data; wherein the extra-oral scanning device is configured to generate dynamic extra-oral maxillofacial data; wherein the processor of the computing device is configured to resolve the intra-oral data with the dynamic extra-oral maxillofacial data to generate a combined data model; wherein the display of the computing device is configured to display a model representation of the dental prosthesis based on the combined data model; wherein the processor is further configured to output manufacturing parameters based on the combined data model; and wherein the manufacturing device is configured to manufacture the dental prosthesis based on the combined data model.

A system which is configured to create an accurate dental prosthesis in-situ, such that patients can walk away with their permanent restoration from only one visit to the dentist can have significant benefits on the health service. By determining manufacturing parameters on a model which combines both intra-oral and dynamic extra-oral data means that the requirement for manual processing of the image can be reduced and, in some instances, completely avoided, helping to realise the intended result of in-situ dental prosthesis manufacturing.

In an optional embodiment, the processor of the computing device is further configured to generate more than one said combined data model; wherein the display is configured to display the more than one said model representation based on the more than one combined data model respectively; and wherein the computing device is further configured to receive an input from a user and select one combined data model based on the selected one model representation.

Beneficially, the intra-oral scanning device may include an oral scanning device with an intra-oral detachable scanning element. This can help dental procedure by allowing detachable scanning elements to be sterilised and re-used whilst another detachable scanning element is in operation. Additionally, or alternatively, the intra-oral scanning device may include two detachable scanning elements or scanners with different operation ranges that scan a single tooth and a full arch of the patient's mandibular teeth and/or maxillary teeth, respectively. This can help reduce the cost of such a system. In a similar vein, the extra-oral scanning device may include an extra-oral detachable scanning element which is compatible with the oral scanning device. The extra-oral scanning device being capable of motion capture and aligning the dynamic extra-oral maxillofacial data with the scans of the single tooth data and full arch.

Beneficially, an assisting computing device may also be provided. In this instance the assistive computing device is in communication with the computing device and is configured to display the or the selected model representation, and to receive an input from an assisting user to amend the combined data model based on the or the selected, model representation. This can act to spread the computing processing across devices. Additionally, an assistive computing device and computing device can be used in parallel to allow a dental technician to make optional amendments to the model representation while a dental surgeon and/or patient can view and possibly amend the model representation on a separate device.

Optionally, the computing device is in communication with a dental record database.

Advantageously, a prototyping device may be provided in communication with the computing device and configured to prototype the model representation or the selected model representation. The prototyping device may be a three-dimensional printer.

According to a third aspect of the invention, there is provided an oral scanning device comprising: a scanner body; and a plurality of detachable scanning elements selectably engagable with the scanner body, wherein one of the plurality of detachable scanning elements is an intra-oral scanning element, and one of the plurality of detachable scanning elements is an extra-oral scanning element.

The provision of an oral scanning device having replaceable heads respectively capable of both intra- and extra-oral scanning techniques allows the above-described method to be implemented simply without needing significant amounts of additional dental equipment.

According to a further aspect of the invention there is provided a method of generating manufacturing parameters during a dental procedure for a dental prosthesis. The method comprises the steps of: a) intra-orally scanning a patient to generate intra-oral data; b) extra-orally scanning the patient during a mandibular motion to generate dynamic extra-oral maxillofacial data; c) resolving the intra-oral data with the dynamic extra-oral maxillofacial data to generate a combined data model; d) generating a model representation of the dental prosthesis based on the combined data model and displaying the model representation to a user; and e) generating manufacturing parameters based on the combined data model.

BRIEF DESCRIPTION OF THE DRAWINGS

For a better understanding of the present invention, and to show more clearly how it may be carried into effect, reference will now be made by way of example only to the accompanying drawings, in which.

DETAILED DESCRIPTION OF THE INVENTION

All publications disclosed and referenced mentioned herein are hereby incorporated herein by reference including priority applications GB2218753.8 filed Dec. 13 2022, and EP22213439.7 filed Dec. 14 2022.

Figure 1:
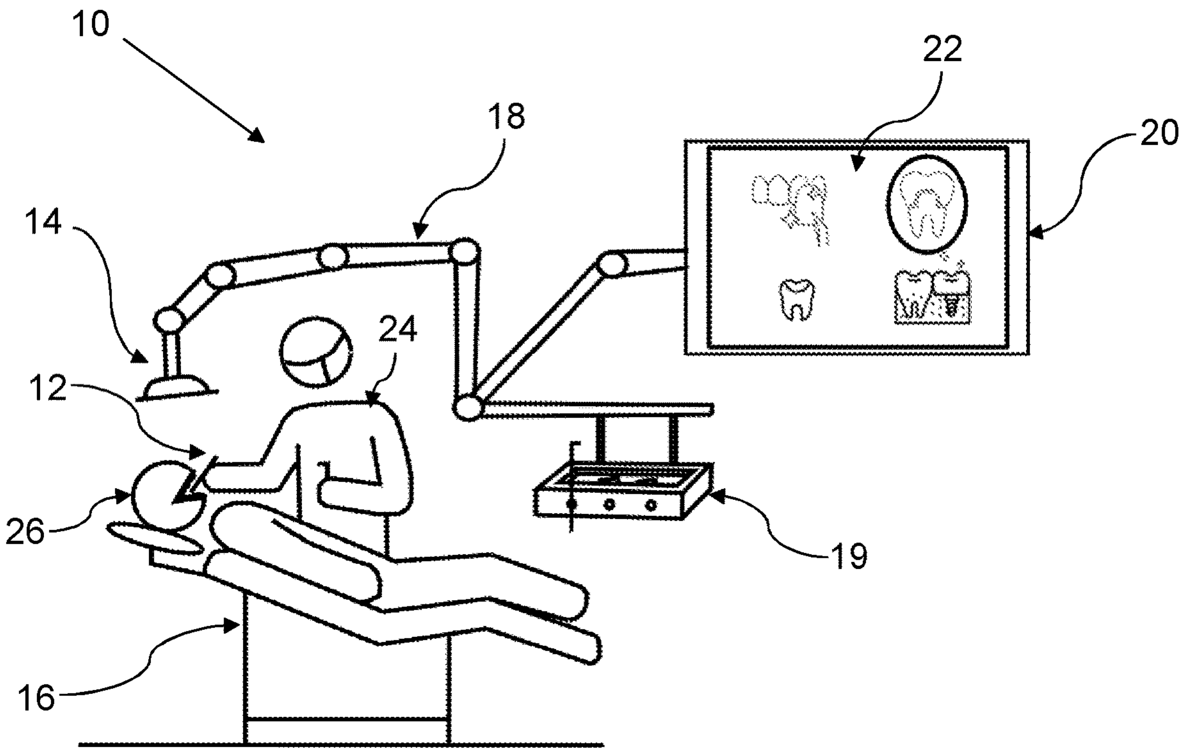
FIG. 1 shows a pictorial representation of one embodiment of an in-situ dental prosthesis manufacturing system in accordance with a second aspect of the invention.

With reference to FIG. 1, there is shown an in-situ dental prosthesis manufacturing system, referenced globally at 10, and which is suitable for the preparation of dental prostheses. This includes, but is not limited to, restorative prostheses such as inlays, onlays, veneers, crowns, fixed partial dentures, implant abutments, and full-mouth reconstructions, but application in orthodontics, maxillofacial treatments and the like are also within the scope of this invention.

The in-situ dental prosthesis manufacturing system 10 comprises a scanning device 12, such as a tooth sensor. In the present embodiment, this is anticipated as being a variable focal-length scanner, having replaceable sensor heads. For example, there may be a primary intra-oral camera body, having intra-oral detachable scanning elements, including a substitutable single tooth sensor head, and a full-arch sensor head. Such a scanning device 12 is used for the acquisition of intra-oral data.

The system 10 further comprises a dental light 14, here shown as an overhead scanning device mounted via an overhead support structure 18 positioned above a dental chair 16. Said overhead support structure 18 may include a support 19 for receiving the scanning device 12.

The intra-oral scanning device may also be capable as acting as an extra-oral scanning device, and which is designed to acquire extra-oral data. In this instance, the intra-oral scanning device may include an oral scanning device with detachable scanning elements. An extra-oral scanning device may be an extra-oral detachable scanning element which is compatible with the oral scanning device of the intra-oral scanning device. It will be appreciated, however, that the extra-oral scanning device 14 may be a larger device, such as a CBCT scanner, and may need to be mounted, for example, via the overhead support structure 18.

In the embodiment shown, the scanning device 12 may comprise a variable focal length scanner lens, acting as an intra-oral scanning device, which captures video, capable of translating to three-dimensional mesh information capture of the full three-dimensional facial structure and/or individual tooth shape and structure. The scanning device 12 may be configured to capture intra-oral three-dimensional anatomy and shade.

This may be provided in the form of a slim, hand-piece sized unit which may be optionally connectable directly to a computing device and/or a dental chair turbine hand-piece console for power and data transfer. A USB connection might be a typical connection means.

The camera end of the scanning device 12 may, as noted above, be replaceable in order to alter the lens type. This allows the scanning device 12 to pick up full arch and/or maxillofacial parameters, as well as providing a close-up lens for high accuracy of tooth scanning. This improves the ability to resolve the intra-oral and extra-oral data sets.

The system 10 further comprises a computing device 20 in communication with both the scanning device 12 and the extra-oral scanning device. The computing device has a display 22 and a processor.

Figure 2:
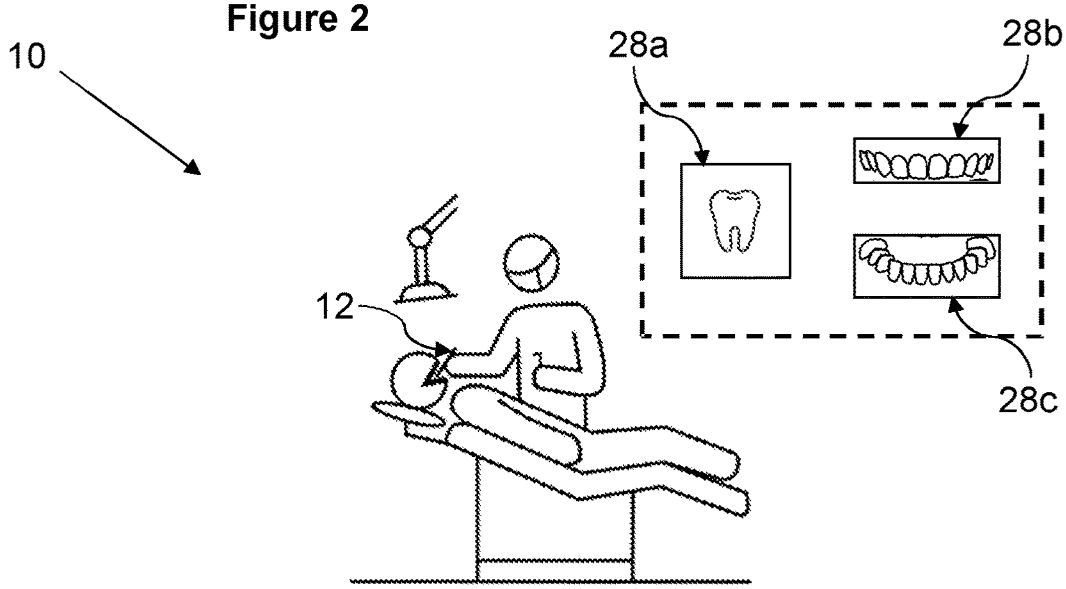
FIG. 2 shows a pictorial representation of a first step of a method of generating manufacturing parameters during a dental procedure for a dental prosthesis in accordance with a first aspect of the invention, using the system of FIG. 1, and more specifically a dental surgeon intra-orally scanning a patient and generating intra-oral data.

Referring now to FIG. 2, a dental surgeon 24 is shown using the in-situ dental prosthesis manufacturing system 10 on a patient 26. The scanning device 12 is used to scan the patient's teeth and jaw and produce intra-oral data.

The intra-oral data in this instance comprises scan data, here illustrated as single tooth data 28*a*, full maxillary teeth arch data 28*b*, and full mandibular teeth arch data 28*c*. The intra-oral data can be reformatted into the form of a digital mould or otherwise into a digital reconstruction of the patient's intra-oral anatomy. In many cases, such intra-oral data is often in the form of a point-cloud, each point in the cloud having three cartesian co-ordinates identifying its location in three-dimensional space.

Whilst three types of scan data are shown, it will be appreciated that only one or combination of two or more scans or part maxillary and or mandibular teeth arch scans may be performed. Furthermore, intra-oral data comprising full or part maxillary and/or mandibular data may be generated by stitching multiple data sources together.

Although intra-oral scanning has been discussed in terms of teeth, soft tissue anatomy may also be captured to inform tooth margins and preparation margins. Intra-oral data generated from full or part maxillary and/or mandibular teeth scans can then be used to help inform contacts with adjacent teeth. Additionally, intra-oral data generated from full or part maxillary and mandibular teeth scans can be used to inform desired occlusion, bite and interference. Intra-oral data may also include data indicative of a patient's tooth colouring.

Figure 3:
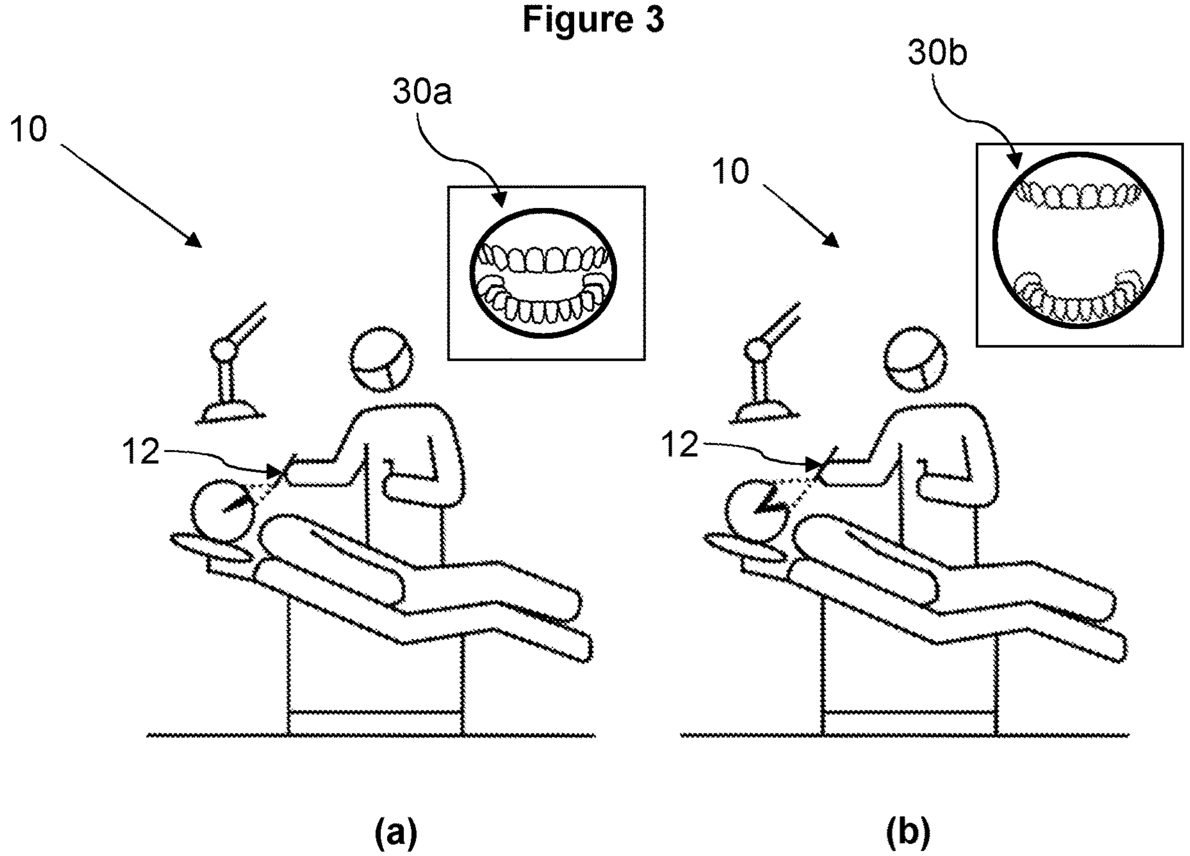
FIG. 3 shows, in sub-Figure (a) a pictorial representation of extra-oral scanning of the patient during a mandibular motion to a closed position, generating dynamic extra-oral maxillofacial data subsequent to the step shown in FIG. 2, whilst sub-Figure (b) shows a pictorial representation of extra-oral scanning of the patient during the mandibular motion to an open position, generating dynamic extra-oral maxillofacial data.

FIG. 3 shows, respectively in sub-Figures (a) and (b), the mandibular motion performed during the process of extra-oral scanning. By moving the mandible, dynamic extra-oral maxillofacial data is generated, as indicated by the first and second maxillofacial scan data 30*a*, 30*b* illustrated in sub-Figures (a) and (b). Extra-oral scanning should also yield facial data, which can be achieved by performing facial recognition on the patient. This facial recognition may be performed on static extra-oral maxillofacial data, rather than on the dynamic data.

Prior to either scanning process, either intra- or extra-oral, the patient can make use of a contrast-improving composition, for example in the form of a chewable tablet or a mouthwash, which improves the definition of the margin between the teeth and the gums.

Figure 4:
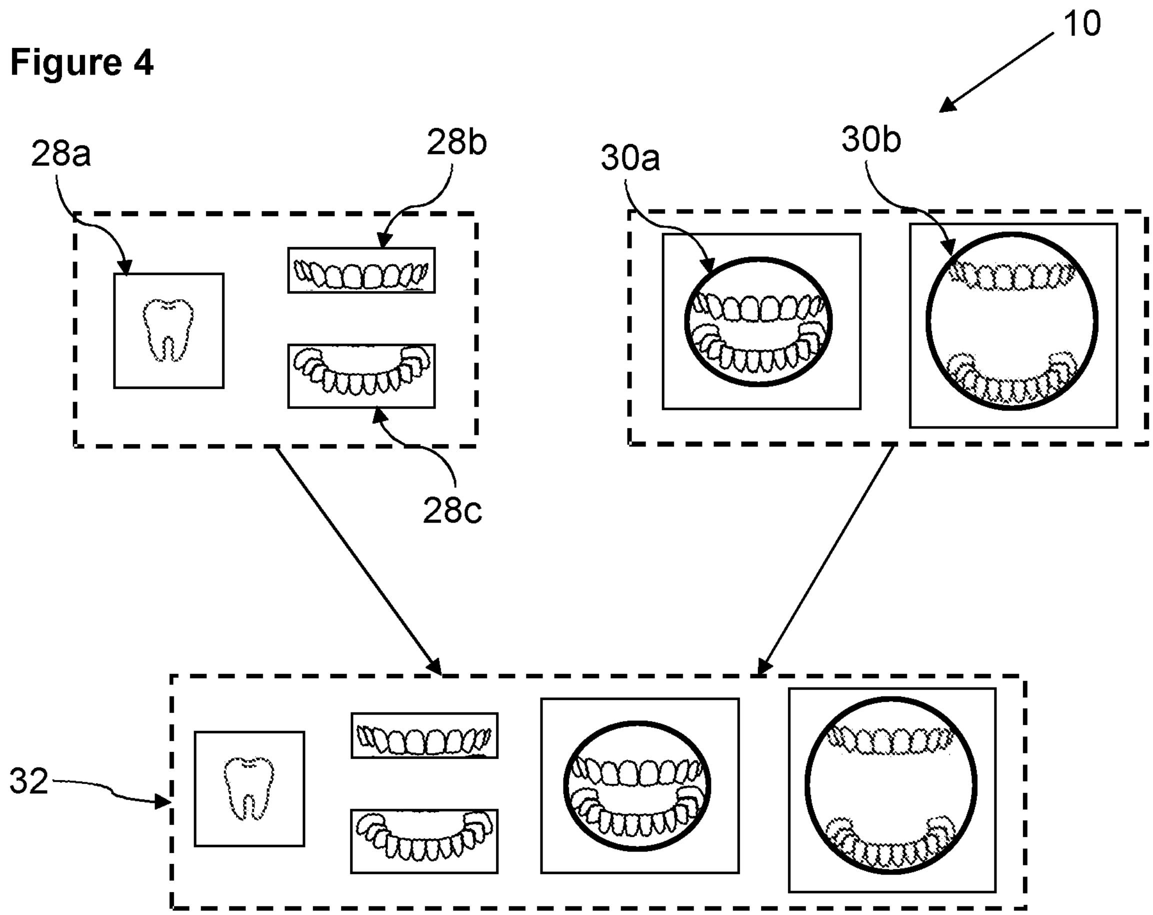
FIG. 4 shows a pictorial representation of a step, subsequent to that of FIG. 3, of resolving the intra-oral data with the dynamic extra-oral maxillofacial data to generate a combined data model.

Once the intra-oral data and extra-oral maxillofacial data have been generated, they can be resolved to generate a combined data model 32. This is represented in FIG. 4. From there, a model representation of a dental prosthesis can be generated. Additionally, or alternatively, it is noted that either the intra-oral data and extra-oral maxillofacial data, but most likely the intra-oral data, can be exported and associated with the standard dental records of the patient. The combined data model 32 could also be associated with the dental records of the patient.

Figure 5:
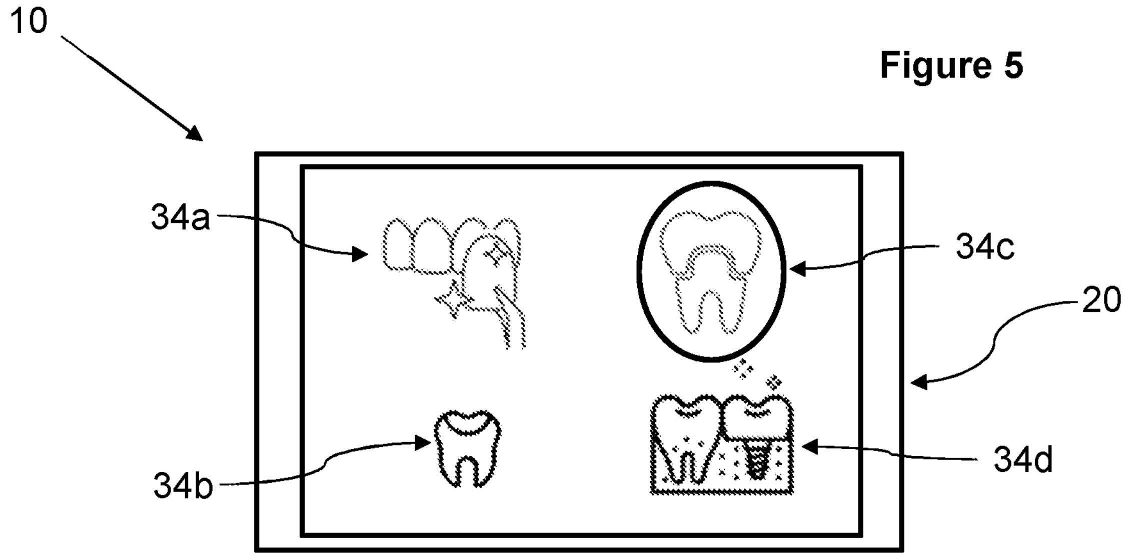
FIG. 5 shows a pictorial representation of a step, subsequent to that of FIG. 4, of selecting a type of dental prosthesis, the types of dental prosthesis including a veneer, a crown, and inlay and an implant.

Prior to the generation of a representation of the dental prosthesis based on the combined data model, there is a preferable step of presenting a plurality of different dental prosthesis types 34*a*, 34*b*, 34*c*, 34*d* to a user on the display 22 of the computing device 20. The user can select a type of dental prosthesis to be manufactured, in the manner shown in FIG. 5 which illustrates the selection of a crown 34*c*. The user may be the patient, dentist, dental surgeon, or dental technician.

Figure 6:
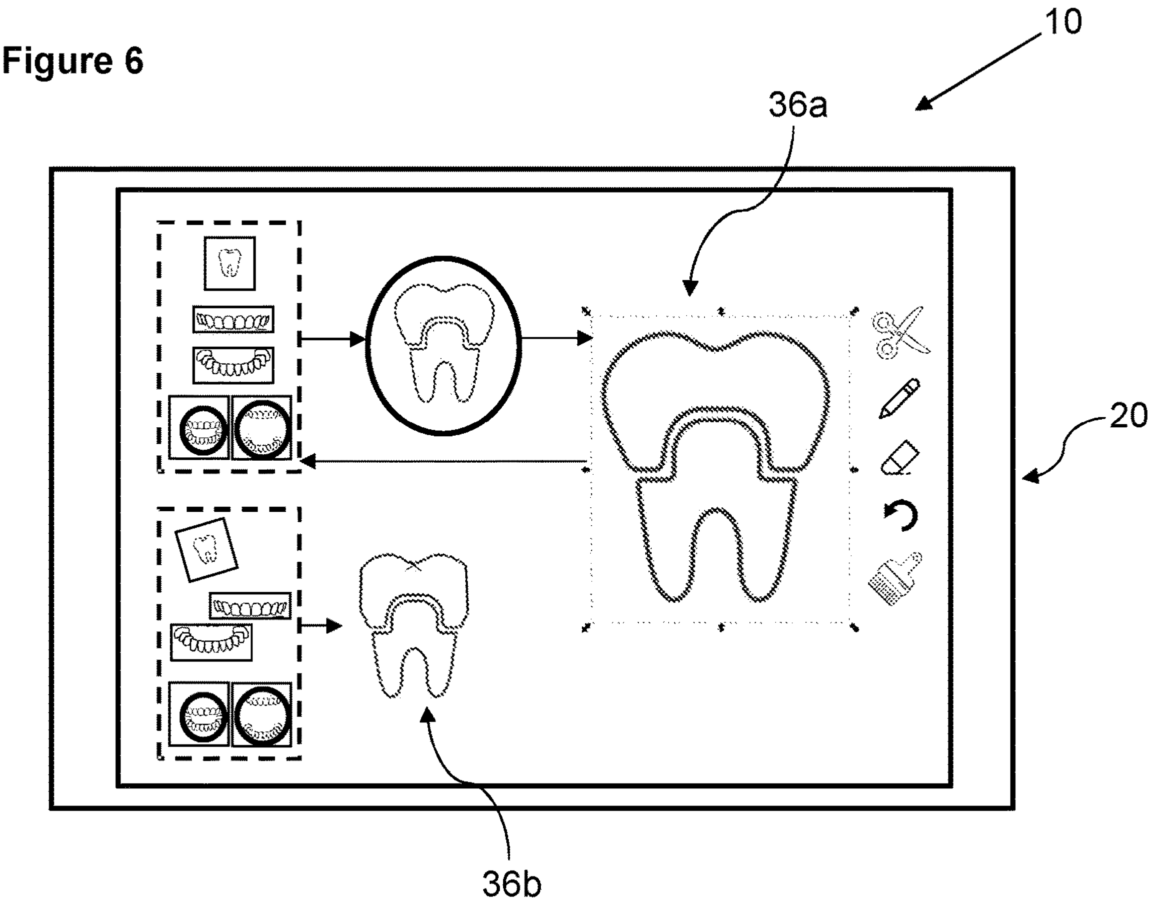
FIG. 6 shows an in-situ dental prosthesis manufacturing system in accordance with a second aspect of the invention, wherein on a display of a computing device of the system, there is a pictorial representation of the process of generating more than one model representation of the dental prosthesis based on more than one combined data model.

This is a powerful feature of the in-situ dental prosthesis manufacturing system 10, in that, preferably by using artificial intelligence or machine learning techniques, the representation of the dental prosthesis can be displayed to the patient, such as in the manner shown in FIG. 6 via the computing device 20. FIG. 6 shows two such representations of the dental prosthesis 36*a*, 36*b* based on two combined data models which are displayed to the patient, dentist, dental surgeon, or dental technician. This may display different tooth characteristics to the user, such as appearance, tooth shape, likely complexity of the dental surgical procedure, need for anaesthetic, cost, and/or longevity, which may influence the decision to be made regarding a selection of the dental prosthesis.

It will be appreciated that the selection of the desired dental prosthesis via the display 22 of the computing device 20 may be performed via a user device, such as a user smartphone. Equally, the computing device 20 could be a device located in the dental surgery, such as a tablet computer, a desktop computer, or even the dental surgeon or technician's own personal device.

The computing device 20 has a workflow thereon which operates as follows. Administrative information may be input, such as patient details, and this may be pre-populated by reception staff within the dental surgery. If the process is managed via a cloud-based server or similar networked machine, then different members of staff may be able to log in to the system to complete different tasks. Administrative information may be presented in terms of a workflow for different types of dental prosthesis, such as veneer, inlay, crown, or bridge. The type of tooth prosthesis to be designed can then also be selected, such as incisor, canine, pre-molar, or molar.

The scanning device 12 or devices can then be coupled to the computing device 20 in a wired or wireless manner, in order to import the intra-oral data and extra-oral maxillofacial data.

The processor of the computing device 20 with then be able to perform the necessary computation to resolve the combined data model.

This will be achieved typically by automatically detecting the preparation margin, thereby defining a bounding region for the combined data model. The intra-oral data can then be automatically merged with the extra-oral maxillofacial data.

In practice, this might be achieved by merging the intra-oral data with face tracking data which is a component of the extra-oral maxillofacial data, creating static composite data. This provides the system with a means of determining the physical static location of the tooth or teeth within the patient's jaw. Once this is complete, the data can be modified further using the dynamic extra-oral maxillofacial data, which provides movement data regarding the static composite data, and thus generating the full combined data model.

The combined data model will be in the form of a CAD mesh, having movement data associated therewith. An automatic artificial intelligence system can then be used to determine bite and jaw movement from the combined data model, and the automatic artificial intelligence system can modify the dental prosthesis design according to an optimised calculated bite and jaw movement. As discussed above, FIG. 6 shows a representation of a display of two possible dental prosthesis options 36*a*, 36*b* for a dental prosthesis having different bite or movement characteristics, both of which being suitable for the patient following the application of the artificial intelligence calculations.

Although a selection of two representations of the dental prosthesis based on two combined data models is shown in FIG. 6, it is appreciated that only one may be generated. Alternatively, more than two representations of the dental prosthesis may be generated for a greater selection. In this instance, the selection may be presented to a user by way of simple on-screen prompts.

The selected representation of the dental prosthesis 36*a* can be manually amended at this stage in the manner shown in FIG. 6. These amendments are then reflected in the associated combined data model.

At this point, suitable manufacturing parameters can be output based on the combined data model. The computing device 20 can automatically export the manufacturing parameters, or can communicate directly with a CAM machine.

Figure 7:
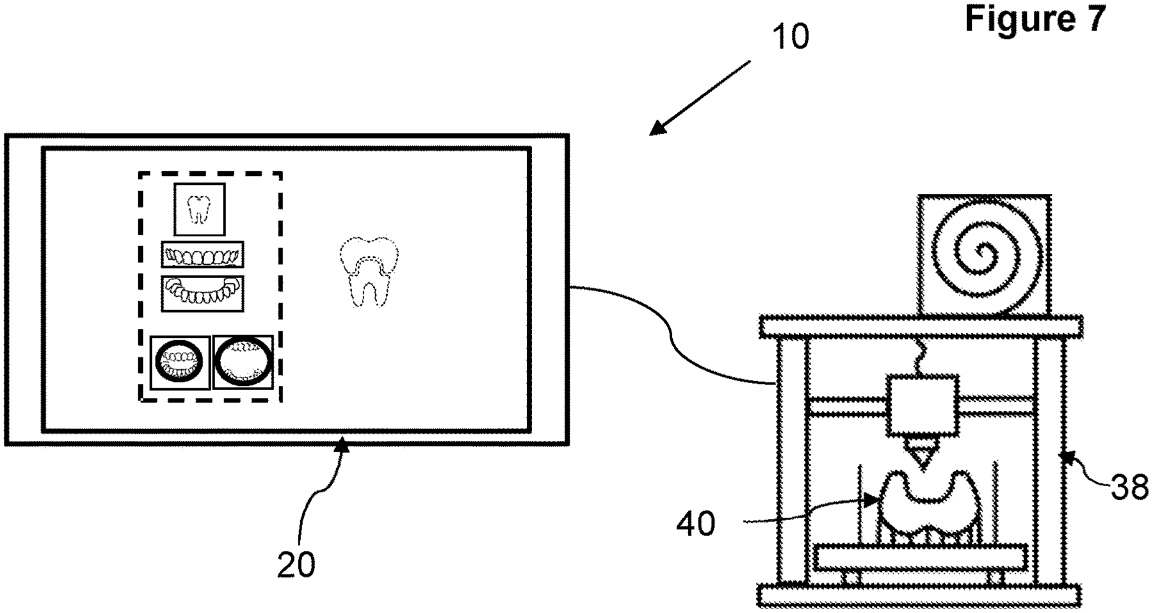
FIG. 7 shows a pictorial representation of the in-situ dental prosthesis manufacturing system of FIG. 6, further comprising a prototyping device.

One powerful option would be to allow the computing device 20 to directly interface with a rapid prototyping machine, as shown in FIG. 7. Typically, this would be an additive manufacturing apparatus 38, such as a 3D printer. This allows for in situ production of a temporary prosthesis, which can be created and installed almost immediately, without any manufacturing lead times. Such prototyping may even be used to inform manual amendments which can be made via the computing device 20.

It is expected that the workflow here would involve 3D printing of the prototype prosthesis 40, followed by a washing process and a resin cure process, to allow for prompt integration of the prototype prosthesis 40 into the patient.

This might be in the innovative form of a new form of 3D printer, in which there are two chambers: a first printing chamber, and a second wash-and-cure chamber. Once printed in the first printing chamber, the prototype prosthesis 40 is transferred via an actuator into the second wash-and-cure chamber. This is the opposite process to standard 3D printers, where the resin is allowed to fast-flow back into the curing layer to provide for improved speed. The advantage here is that the dental surgeon or technician need never come into contact with wet resin, thereby avoiding contamination.

Figure 8:
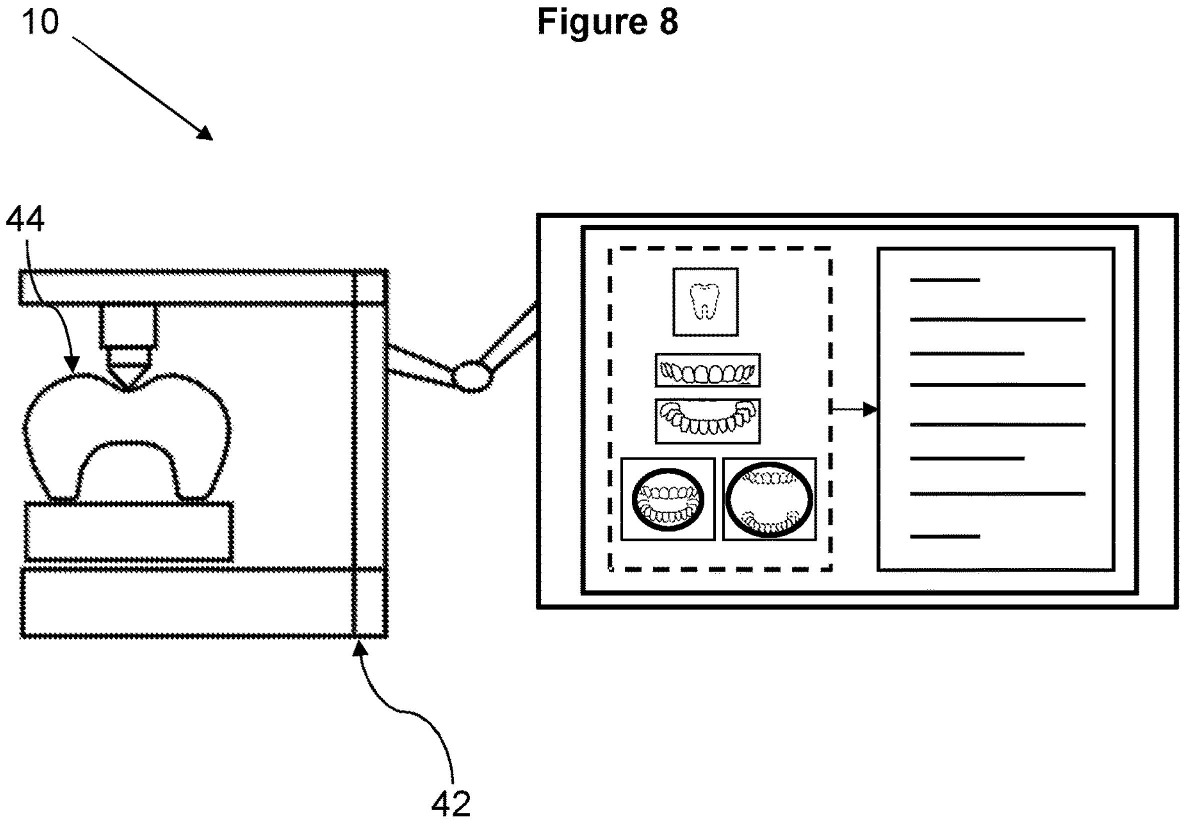
FIG. 8 shows a pictorial representation of the in-situ dental prosthesis manufacturing system of FIG. 6, further comprising a manufacturing device.

All while this process is underway, the manufacturing parameters can also be exported, as shown in FIG. 8, to a standard CAM machine 42, which may be offsite, to allow for precision milling and manufacture of the final dental prosthesis 44. The patient can return at some point in the future to have their temporary prototype prosthesis 40 replaced with the more hard-wearing final dental prosthesis 44. However, the rapid manufacturing aspect of the present invention provides for a workflow in which there is no lag time where the patient has no prosthesis.

Figure 9:
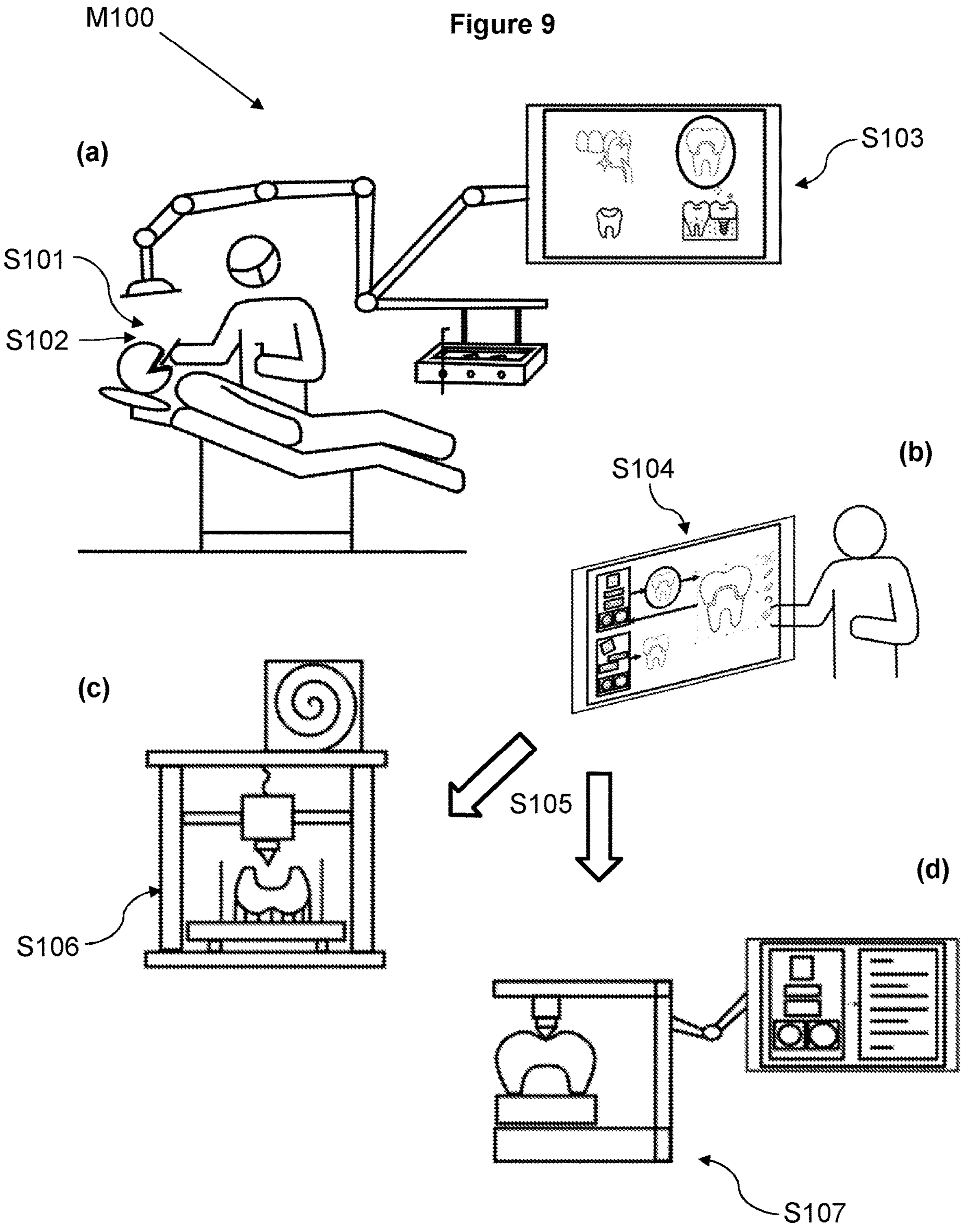
FIG. 9 shows a pictorial representation of a complete method of generating manufacturing parameters during a dental procedure for a dental prosthesis in accordance with the first aspect of the invention.

FIG. 9 shows a summary of the methodology used in the present invention. There is a method M100 of generating manufacturing parameters during a dental procedure for a dental prosthesis, the method comprising the steps of: a) intra-orally scanning, at step S101, a patient to generate intra-oral data; b) extra-orally scanning, at step S102, the patient during a mandibular motion to generate dynamic extra-oral maxillofacial data; c) resolving the intra-oral data, at step S103, with the dynamic extra-oral maxillofacial data to generate a combined data model; d) generating, at step S104, a model representation of the dental prosthesis based on the combined data model and displaying the model representation to a user; and e) generating manufacturing parameters, at step S105, based on the combined data model. The manufacturing parameters can be used in situ for rapid prototyping in the dental surgery, at step S106, and meanwhile, the manufacturing parameters can be used to prepare a more detailed bespoke dental prosthesis, at step S107, for subsequent implantation.

It will be apparent that, whilst the term dental prosthesis is used primarily in relation to tooth implants or similar, that orthodontic inserts, such as alignment tools or braces, could equally be designed in situ using the system described above.

Furthermore, whilst the control of the workflow from a device-level perspective has been illustrated as being via a single computing device, it will be appreciated that there could be non-centralised data engagement across several devices.

It is therefore possible to provide a method of generating manufacturing parameters during a dental procedure for a dental prosthesis such that a patient can receive a permanent dental prosthesis the same day or during the same procedure. Additionally, it is also possible to provide an in-situ dental prosthesis manufacturing system.

The words 'comprises/comprising' and the words 'having/including' when used herein with reference to the present invention are used to specify the presence of stated features, integers, steps, or components, but do not preclude the presence or addition of one or more other features, integers, steps, components, or groups thereof.

It is appreciated that certain features of the invention, which are, for clarity, described in the context of separate embodiments, may also be provided in combination in a single embodiment. Conversely, various features of the invention which are, for brevity, described in the context of a single embodiment, may also be provided separately or in any suitable sub-combination.

The embodiments described above are provided by way of example only, and various changes and modifications will be apparent to persons skilled in the art without departing from the scope of the present invention as defined by the appended claims

The invention claimed is:

1. A method of generating manufacturing parameters during a dental procedure for a dental prosthesis, the method comprising the steps of:

a) intra-orally scanning a patient to generate intra-oral data using a scanning device having a plurality of detachable and interchangeable scanning heads including an intra-oral scanning head and an extra-oral scanning head; whereby the intra-oral scan data forms a high-resolution geometric mesh, b) extra-orally scanning the patient during a mandibular motion using the extra-oral scanning head of the same scanning device to generate dynamic extra-oral maxillofacial motion data;

c) resolving the intra-oral data with the dynamic extra-oral maxillofacial motion data to generate a combined data model comprising a three-dimensional geometric mesh of the intra-oral data having mandibular motion data associated therewith, wherein resolving comprises aligning the intra-oral data with extra-oral facial data to establish a spatial reference frame and applying the mandibular motion data to the geometric mesh within the same spatial reference frame to generate a dynamic occlusion model; whereby static intra-oral morphology is resolved with dynamic facial motion capture to generate manufacturing parameters derived from functional mandibular movement, rather than solely on static occlusion;

d) generating a model representation of the dental prosthesis based on the combined data model and displaying the model representation to a user; and e) generating manufacturing parameters based on the combined data model such that the manufacturing parameters are generated directly from the dynamic occlusion model.

2. The method of claim 1, wherein during step c), more than one said combined data model is generated; wherein during step d), more than one said model representation of the dental prosthesis is generated based on each of the more than one combined data models respectively; further comprising a step after step d) and before step e), of selecting one representation of the dental prosthesis; and wherein during step e), manufacturing parameters are generated based on the combined data model of the selected one representation.

3. The method of claim 1, further comprising a step after step d) and before step e), of amending the combined data model based on amendments made to the model representation or the selected one representation of the dental prosthesis displayed to the user.

4. The method of claim 1, wherein during step b), the mandibular motion is facilitated by a contrast-enhancing medium.

5. The method of claim 1, wherein during step a), the generation of intra-oral data includes intra-orally scanning a single tooth of the patient.

6. The method of claim 1, wherein during step a), the generation of intra-oral data includes intra-orally scanning a full arch of the patient's mandibular teeth and/or maxillary teeth.

7. The method of claim 1, wherein step b), further includes extra-orally scanning the patient while a mandible of the patient is in a closed position to generate static extra-oral maxillofacial data; and during step c) the combined data model is based on resolving the intra-oral data with both the dynamic and static extra-oral maxillofacial data.

8. The method of claim 1, further comprising a step before step e), of prototyping the model representation or the one selected model representation of the dental prosthesis.

9. A method as claimed in claim 1, wherein the scanning device comprises a plurality of interchangeable scanning heads including a first scanning head configured for single-tooth intra-oral scanning, a second scanning head configured for full-arch intra-oral scanning, and a third scanning head configured for extra-oral maxillofacial scanning.

10. A method as claimed in claim 1, wherein the method is performed in a single clinical session at chairside, and wherein the manufacturing parameters are generated in-situ during the dental procedure for immediate manufacture of the dental prosthesis.

11. The method of claim 1, wherein resolving the intra-oral data with the dynamic extra-oral maxillofacial motion data comprises first merging the intra-oral data with static extra-oral facial data to generate a static composite model, and subsequently modifying the static composite model using the dynamic extra-oral maxillofacial motion data to generate the combined data model.

12. The method of claim 1, wherein the combined data model comprises a computer-aided design (CAD) mesh having mandibular motion data mapped thereto such that the CAD mesh is dynamically transformable in response to the mandibular motion data.

13. The method of claim 1, wherein aligning the intra-oral data with extra-oral facial data comprises merging the intra-oral data with face tracking data to determine a physical spatial position of the intra-oral data within the patient's jaw.

14. The method of claim 1, wherein the scanning device comprises a variable focal-length scanner having interchangeable sensor heads configured to selectively capture full-arch intra-oral data and single-tooth intra-oral data.

15. The method of claim 1, wherein resolving the intra-oral data with the dynamic extra-oral maxillofacial motion data comprises automatically detecting a preparation margin to define a bounding region for the combined data model prior to generation of the model representation.

16. The method of claim 1, wherein the dynamic occlusion model is used by an automated system to determine bite and jaw movement and to modify the model representation of the dental prosthesis based on an optimized calculated bite.

17. The method of claim 1, wherein the manufacturing parameters are used to generate a prototype dental prosthesis using an additive manufacturing device and to generate a final dental prosthesis using a separate manufacturing device.

18. The method of claim 1, wherein the plurality of detachable and interchangeable scanning heads include an intra-oral head, a substitutable single tooth sensor head, and a substitutable full-arch sensor head.

19. The method of claim 1, wherein at least one of the plurality of detachable and interchangeable scanning heads comprises a camera wherein the camera is interchangeable in order to alter the lens type wherein said lens type may be selected to specifically visualize a full arch and/or maxillofacial parameter or a close-up of a single tooth.

* * * * *